(12) United States Patent
Chia et al.

(10) Patent No.: US 6,233,477 B1
(45) Date of Patent: May 15, 2001

(54) CATHETER SYSTEM HAVING CONTROLLABLE ULTRASOUND LOCATING MEANS

(75) Inventors: Weng-Kwen Raymond Chia, Irvine; Hosheng Tu, Tustin, both of CA (US)

(73) Assignee: Irvine Biomedical, Inc., Irvine, CA (US)

( * ) Notice: Subject to any disclaimer, the term of this patent is extended or adjusted under 35 U.S.C. 154(b) by 0 days.

(21) Appl. No.: 09/370,603

(22) Filed: Aug. 9, 1999

Related U.S. Application Data

(63) Continuation-in-part of application No. 08/954,001, filed on Oct. 20, 1997, now Pat. No. 5,954,649.

(51) Int. Cl.[7] ....................................................... A61B 5/05
(52) U.S. Cl. .......................................... 600/424; 607/122
(58) Field of Search ................................. 600/407, 424, 600/437, 373; 607/122

(56) References Cited

U.S. PATENT DOCUMENTS

| | | | |
|---|---|---|---|
| 5,480,422 | * 1/1996 | Ben-Haim | 607/122 |
| 5,722,402 | * 3/1998 | Swanson et al. | 607/122 |
| 5,735,280 | * 4/1998 | Sherman et al. | 601/2 |
| 5,840,031 | * 11/1998 | Crowley | 600/440 |
| 5,868,673 | * 2/1999 | Vesely | 600/407 |
| 5,954,649 | * 9/1999 | Chia et al. | 600/424 |

* cited by examiner

Primary Examiner—Brian L. Casler

(57) ABSTRACT

An improved catheter system having ultrasound locating capabilities comprising a locator catheter and an ultrasound receiver catheter resulting in an effective electrophysiology procedure without undesired side effects of using a conventional x-ray imaging system. Said catheter system comprising a locator catheter consisted of at least one electrode and an ultrasound crystal secured on the locator catheter; and a reference catheter comprising three or more ultrasound crystal beacons which have pre-determined locations with reference to an external locating calibration system, wherein said external locating calibration system constantly calibrates the coordinates of the beacons on the reference catheter, having at least one ultrasound beacon is movable/controllable by a beacon deployment means.

16 Claims, 8 Drawing Sheets

CATHETER SYSTEM HAVING CONTROLLABLE ULTRASOUND LOCATING MEANS

CROSS-REFERENCE TO RELATED APPLICATIONS

This application is a continuation-in-part of application Ser. No. 08/954,001, filed Oct. 20, 1997, now U.S Pat. No. 5,954,649.

FIELD OF THE INVENTION

The present invention generally relates to improved constructions for a catheter system. More particularly, this invention relates to catheters and methods for mapping cardiac arrhythmias and ablative cardiac tissues via a steerable catheter system having ultrasound locating capabilities, comprising a locator catheter and an ultrasound receiver catheter having location-controllable transducers, resulting in an effective electrophysiology procedure without undesired side effects of using a conventional x-ray imaging system.

BACKGROUND OF THE INVENTION

Symptoms of abnormal heart rhythms are generally referred to as cardiac arrhythmas, with an abnormally rapid rhythm being referred to as a tachycardia. The present invention is concerned with the treatment of tachycardias which are frequently caused by the presence of an "arrhythmogenic site" or "accessory atrioventricular pathway" close to the inner surface of the chambers of a heart. The heart includes a number of nonnal pathways which are responsible for the propagation of electrical signals from the upper to the lower chambers necessary for performing normal systole and diastole function. The presence of arrhythmogenic site or accessory pathway can bypass or short circuit the normal pathway, potentially resulting in very rapid heart contractions, referred to herein as tachycardias.

Treatment of tachycardias may be accomplished by a variety of approaches, including drugs, surgery, implantable pacemakers/defibrillators, and catheter ablation. While drugs may be the treatment of choice for many patients, they only mask the symptoms and do not cure the underlying causes. Implantable devices only correct the arrhythmia after it occurs. Surgical and catheter-based treatments, in contrast, will actually cure the problem, usually by ablative the abnormal arrhythmogenic tissue or accessory pathway responsible for the tachycardia. It is important for a physician to accurately steer the catheter to the exact site for ablation. Once at the site, it is important for a physician to control the emission of energy to ablate the tissue within the heart.

Of particular interest to the present invention are radiofrequency (RF) ablation protocols which have proven to be highly effective in tachycardia treatment while exposing a patient to minimal side effects and risks. Radiofrequency catheter ablation is generally performed after conducting an initial mapping study where the locations of the arrhythmogenic site and/or accessory pathway are determined. After a mapping study, an ablation catheter is usually introduced to the target heart chamber and is manipulated so that the ablation tip electrode lies exactly at the target tissue site. Radiofrequency energy or other suitable energy is then applied through the electrodes to the cardiac tissue in order to ablate the tissue of arrhythmogenic site or the accessory pathway. By successfully destroying that tissue, the abnormal signal patterns responsible for the tachycardia may be eliminated.

The mapping and ablation procedures require means to locate the catheter, especially the tip section of said catheter, to the exact site of the arrhythmogenic sources. The conventional method uses x-ray fluoroscope to image the location of the catheter. While x-ray imaging is quite successful, some patients, such as the pregnant women, the fluorophobic patients and the like, can tolerate little x-ray exposure. It is imperative that other imaging means be used to locate the catheter within the body of a patient.

Ultrasound imaging has been used extensively to reveal the existence of a device having the ultrasound emitter. In the U.S. Pat. No. 4,794,931, there has been disclosed a catheter and system which can be utilized for ultrasonic imaging. However, there is no disclosure on the technique of using ultrasound locating means to generate the three-dimensional location data. Based on recent advances in computer data analysis capability, the speed of analyzing the data obtained from a 3-D ultrasound locating system becomes feasible.

Though a 3-D ultrasound locating system is useful, sometimes one of the multiple signal receivers may approximately overlap on the other signal receiver so that the locating capability is compromised. To alleviate this potential weakness, a location-controllable signal receiver of ultrasound transducers that are movable with known location coordinates becomes important.

While an electrophysiology mapping and/or ablation procedure using an existing catheter has had promising results under x-ray imaging, reduction or elimination of x-ray exposure becomes a clinical need and a health issue to certain types of patients undergoing the catheter-based treatment. Therefore there is a need for an improved catheter system having ultrasound locating capabilities that comprises a location-controllable signal means for optimizing the 3-D locating of a catheter system.

SUMMARY OF THE INVENTION

In general, it is an object of the present invention to provide an improved catheter system for positioning the mapping and/or ablation catheter. It is another object of the present invention to provide a catheter system having the capability to generate three-dimensional location coordinates for the mapping and/or ablation catheter. It is still another object of the present invention to provide a catheter system using the ultrasound locating technique that comprises at least one location-controllable signal receiver of ultrasound transducers that are movable with known location three-dimensional coordinates. It is another object of the present invention to provide a catheter system with ultrasound receiving means inserted in the body of a patient for three-dimensional locating capabilities. It is another object of the present invention to provide a catheter system with ultrasound receiving means external of the body of a patient for three-dimensional locating capabilities.

It is still another object of the present invention to provide a catheter system comprising a locator catheter and a reference receiver catheter, wherein a plurality of ultrasound crystal beacons are secured on said catheters having emitting and receiving ultrasonic signals capabilities. In one embodiment, at least one ultrasound crystal is secured on the locator catheter and at least three crystals are secured on the reference catheter. To further identify and calibrate the location of the locator catheter, at least four crystals are secured on the reference catheter in an alternate embodiment. At least one crystal beacon is movable by a beacon deployment mechanism at the handle, said ultrasound crystal beacons having coordinates that are pre-set with reference to an external location calibration system, wherein said beacons can emit and receive ultrasound signals.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

The catheter system of the present invention is consisted of a reference catheter serving as a receiver for ultrasound signals and a locator catheter serving as the mapping and/or ablation catheter which has the capability of emitting ultrasound signal. Both catheters have the capabilities of emitting and receiving ultrasound signals, which can be translated to digital data to be analyzed and stored by data acquisition means.

The locator catheter is a standard electrophysiology catheter comprising an additional ultrasound crystal, which is made of piezoelectric materials. Said ultrasound crystal can vibrate at an ultrasound frequency by giving a voltage impulse, or delivering an electric energy by receiving resonant ultrasound vibration. Thus, it can function as either a transmitter or a receiver. The data can be relayed to a data acquisition device for storage and analysis.

The reference catheter comprises a plurality of ultrasound crystals as "beacon". In one embodiment, the reference catheter comprises three or more ultrasound beacons which have pre-determined locations or three-dimensional coordinates with reference to an external locating calibration system. The crystals used in ultrasound imaging means can be shaped as a cylinder, a donut, a ring, a spiral, a mesh, or other appropriate shape. The crystals can be located on different apparatus or means to provide three-dimensional coordinates. The crystal is made of piezoelectric materials and has a conducting means to transmit the signal in either way for emitting or for receiving. In on embodiment, at least one ultrasound beacon is moveable on the reference catheter and deployable/controllable by a beacon deployment mechanism, which may comprise a push-pull mechanism, located at a handle of the catheter. Said movable ultrasound beacon comprises a location-controllable signal means for optimizing the 3-D locating of a catheter system.

Figure 1:
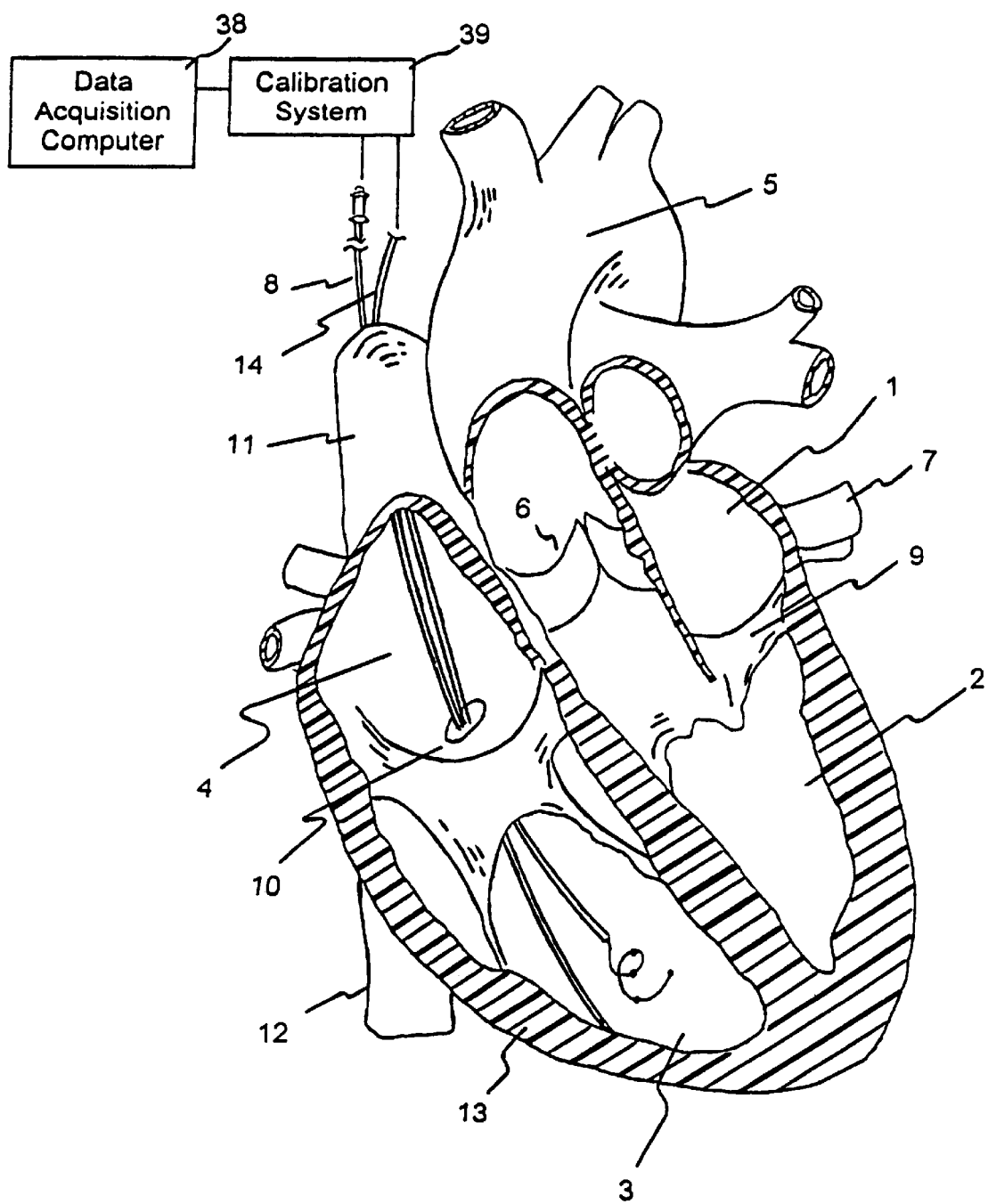
FIG. 1 is a perspective view of a catheter system having a locator catheter and a reference catheter under deployed state constructed in accordance with the principles of the present invention.

FIG. 1 shows a perspective view of the catheter system in a chamber of a heart under a deployed state. The heart has a left atrium 1, a left ventricle 2, a right ventricle 3, and a right atrium 4. An aorta 5 connects with the left ventricle 2 and contains the aorta valve 6. A pulmonary artery 7 connects with the right ventricle 3. The left atrium 1 communicates with the left ventricle 2 through a mitral valve 9. The right atrium 4 communicates with the right ventricle 3 through a tricuspid valve 10. Superior vena cava 11 and inferior vena cava 12 lead into the right atrium 4. A myocardial wall 13 separates the left and right ventricles. A locator catheter 8 and a reference catheter 14 are shown passing through the superior vena cava 11, the tricuspid valve 10 into the right ventricle 3.

Figure 2:
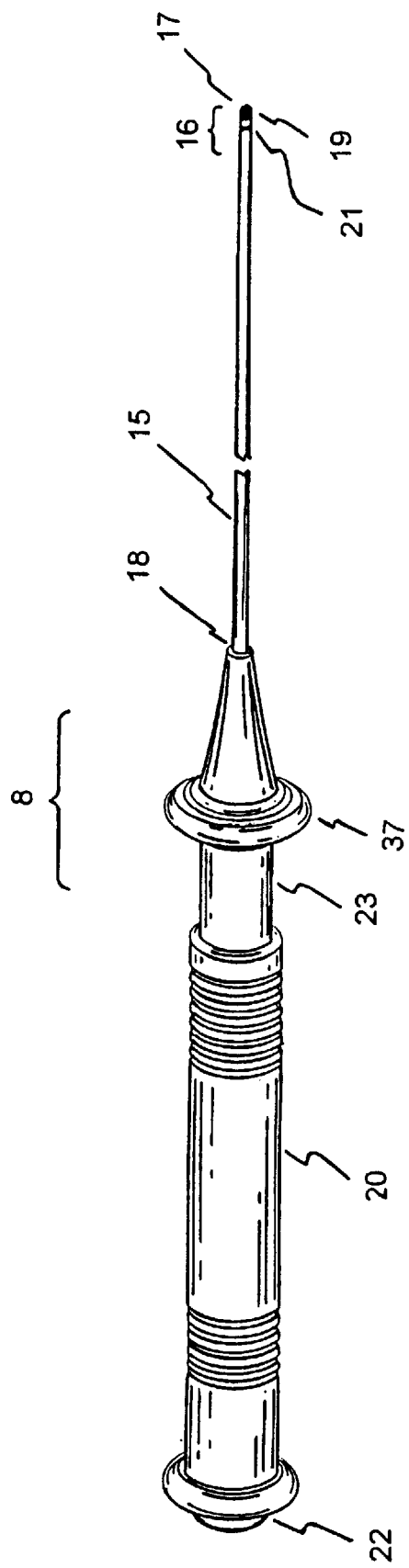
FIG. 2 is an overall view of the locator catheter having an ultrasound crystal at its tip section

FIG. 2 is an overall view of the locator catheter having an ultrasound crystal at its tip section. In one embodiment, a locator catheter 8 comprises a catheter shaft 15 having a distal tip section 16, a distal end 17, a proximal end 18 and at least one lumen extending therebetween, wherein at least one electrode 19 is secured at said distal tip section 16. A handle 20 is attached to the proximal end 18 of said catheter shaft 15. An ultrasound crystal 21 is secured on the catheter shaft proximal to the distal end 17. A connector 22 is usually attached to the proximal end of said handle 20. As a steerable catheter, a push-pull mechanism 23 is located on the handle. In another embodiment, the catheter comprises at least one temperature sensor and an external close-loop temperature control means. In an alternate embodiment, the at least one electrode 19 can be a cylindrical tip electrode, a ring electrode, a spiral electrode, or a mesh electrode.

The crystal 21 on the locator catheter 8 emits repeated signals at a pre-determined time period of fixed frequency, say e.g. at 20 kHz, to be received by the beacons of the reference catheter or an external receiving station. The frequency can be changed to signify the sequence of the signals emission. The ultrasound waves, traveling at a constant speed, reach the three or more beacons at different time. Thus the distance between the crystal on the locator catheter and any beacon on the reference catheter can be calculated as $d_1 = v \times t_1$, where "$d_1$" is the distance between the crystal and the beacon no. 1, "v" is the known ultrasound velocity, and "$t_1$" is the traveling time of the ultrasound from the crystal on the locator catheter to the beacon no. 1. The exact location of the tip of the locator catheter can be determined by the distances between it and the three or more of the beacons on the reference catheter, where the exact coordinates of the beacons on the reference catheter is pre-set or pre-determined with reference to an external location calibration means. In another embodiment, the locator catheter comprises a plurality of ultrasound crystals to locate the whole tip section of said catheter.

The ultrasound frequency employed in this invention is selected from the range that its biological effects on the surrounding tissues or to the body of a patient are considered negligible.

Figure 3:
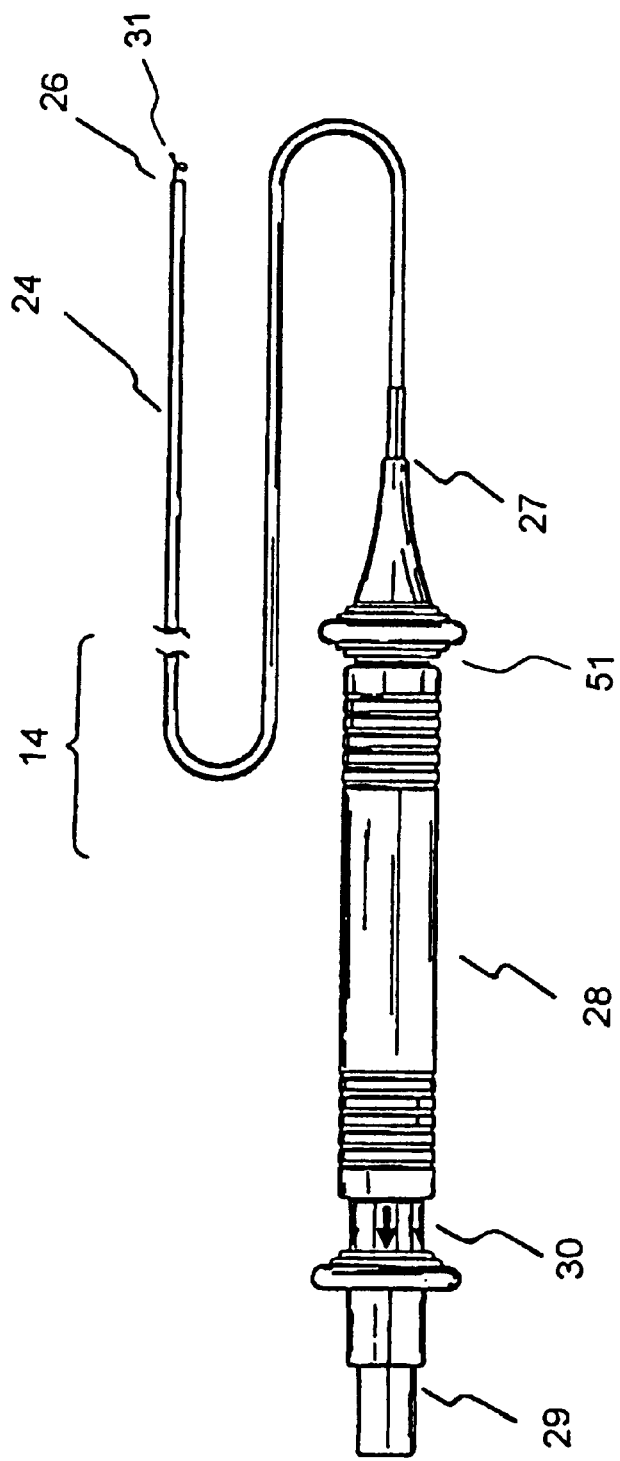
FIG. 3 is an overall view of the reference catheter under a non-deployed state.

FIG. 3 is an overall view of a reference catheter under a non-deployed state. In one embodiment, the reference catheter 14 comprises a delivery shaft 24 and a spiral element 25 (shown on FIG. 4), wherein the spiral element stays within the delivery shaft under a non-deployed state. The delivery shaft 24 having a distal end 26, a proximal end 27 and at least one lumen extending therebetween. A handle 28 is attached to the proximal end 27 of said delivery shaft 24. A connector 29 is usually secured to the proximal end of said handle 28. During catheter insertion into and removal from the body of a patient, the reference catheter 14 is under a non-deployed state. After the reference catheter is advanced to the target ventricle or the atrium, the spiral element 25 is deployed. The element deployment can be achieved by a pushing action at a push-pull mechanism 30 on the handle 28. A beacon deployment mechanism 51 is also mounted at the handle 28 for moving/controlling the at least one movable beacon 31 on the reference catheter 14.

Figure 4:
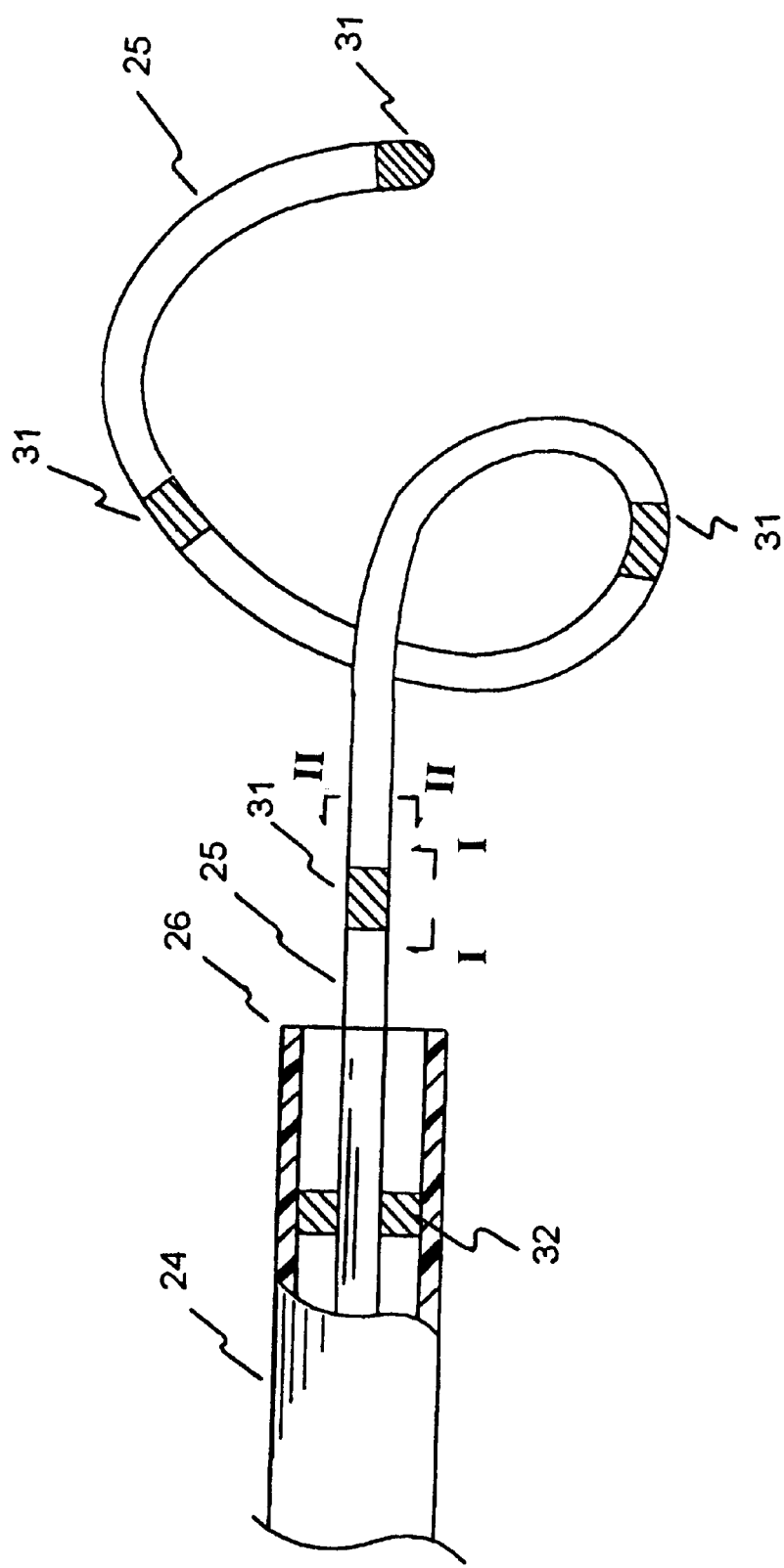
FIG. 4 is a close-up view of a reference catheter having a controllable ultrasound crystal beacon under a deployed state.

FIG. 4 shows the distal section of a reference catheter under a deployed state. The pre-shaped spiral element 25 comprises three or more crystal beacons 31 that have the capability to emit and receive ultrasound signals. At least one crystal beacon is movable and controllable by a beacon deployment mechanism 51. Their locations on the spiral element are preferably to form the three corners of a pyramid whereas the fourth corner is an ultrasound crystal on the locator catheter 8. In another embodiment, said reference catheter is designed as a spiral wire with crystals located strategically 120 degree apart in the case of three beacons system, or 90 degree apart in another case of four beacons system. A silicone type check valve 32 is installed at certain opening of the lumen of the catheter shaft 24.

Figure 5:
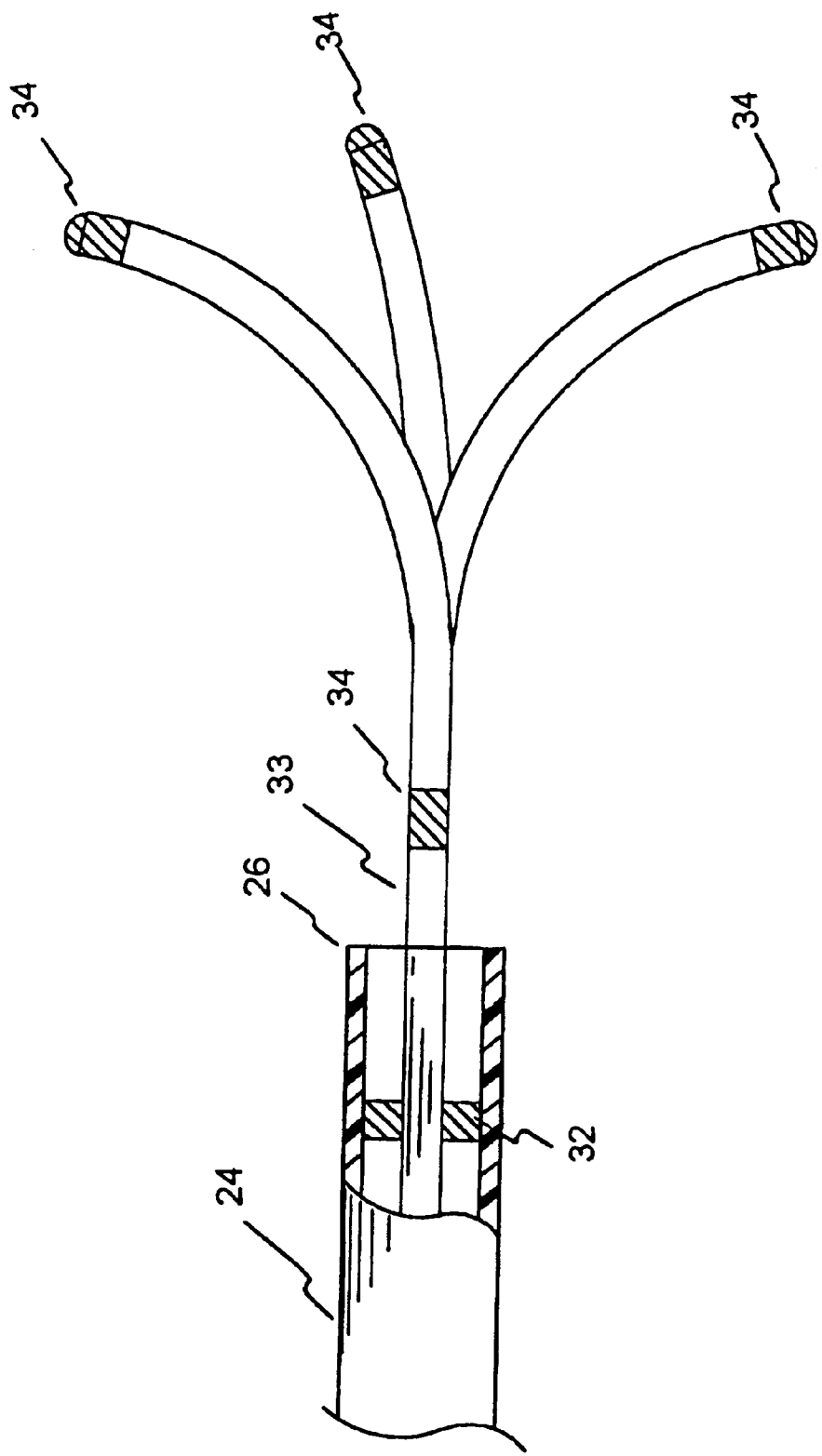
FIG. 5 is a close-up view of an alternate reference catheter under a deployed state.
Figure 6:
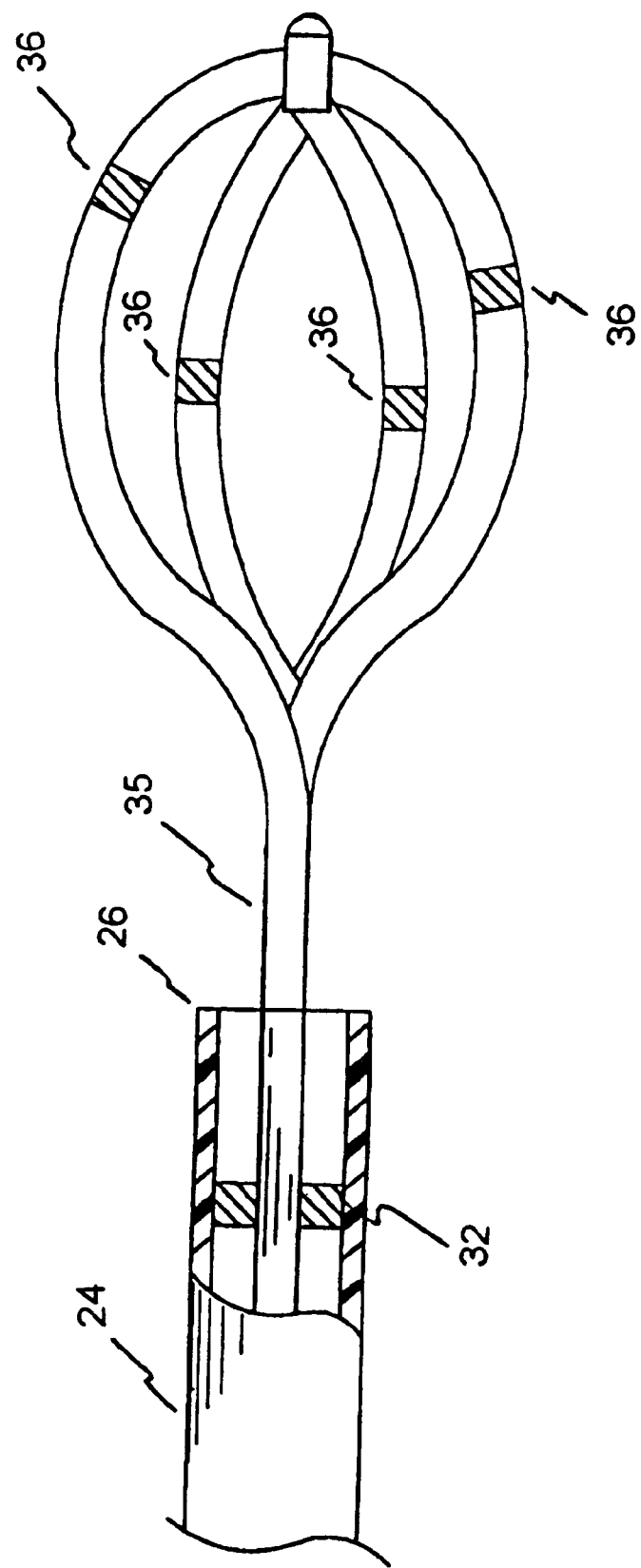
FIG. 6 is a close-up view of still an other a lternate reference catheter under a deployed state.

FIG. 5 shows a close-up view of the distal section of an alternate reference catheter under a deployed state. The pre-shaped forky element 33 comprises three or more crystal beacons 34 that have the capability to emit and receive ultrasound signals. Similarly, at least one crystal beacon is movable and controllable by a beacon deployment mechanism 51. In a further embodiment, FIG. 6 shows a close-up view of still another alternate reference catheter under a deployed state. The pre-shaped basket element 35 comprises three or more crystal beacons 36 that have the capability to emit and receive ultrasound signals. At least one crystal beacon is movable and controllable by a beacon deployment mechanism 51.

Figure 7:
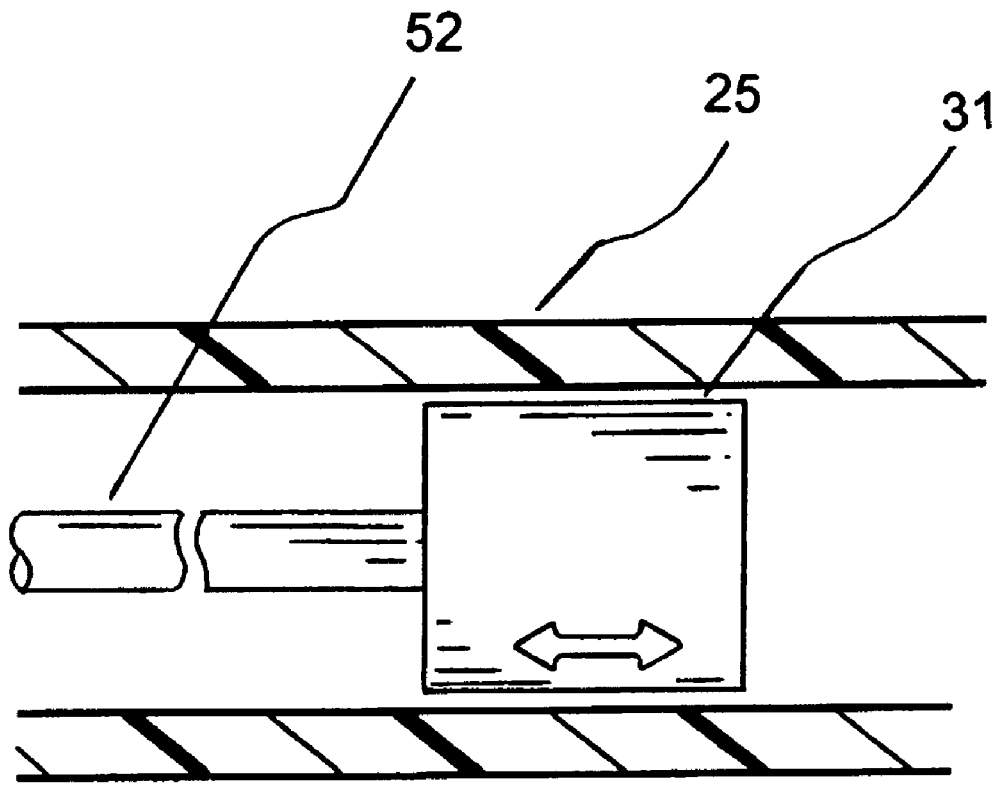
FIG. 7 is a longitudinal cross-sectional view of the controllable ultrasound crystal beacon portion, section I—I, of FIG. 4.

FIG. 7 shows a longitudinal cross-sectional view of the controllable ultrasound crystal beacon portion, section A—A, of FIG. 4. In one embodiment, a movable crystal beacon 31 is connected to the beacon deployment mechanism 51 through a connecting means 52 for transmitting the deployment force to the movable beacon 31. The connecting means 52 may be a flat wire, a flexible tubing, or a flexible rod that has torque transmission capabilities. The exact distance of the beacon movement of movable beacon 31 on the reference catheter 14 is correlated to the deployment degree of the beacon deployment mechanism 51. This is to alleviate a potential weakness that sometimes one of the crystal beacons may approximately overlap on the other crystal beacon so that the locating capability is compromised. A location-controllable movable crystal beacon 31 is deployable with known location coordinates.

Figure 8:
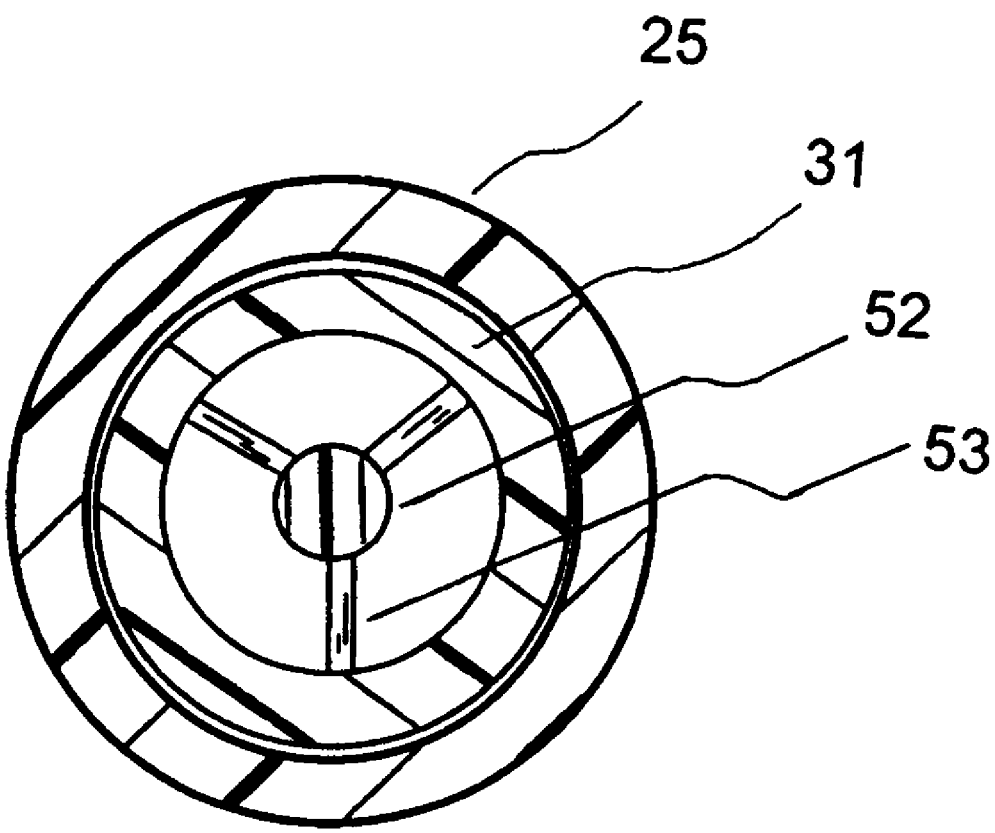
FIG. 8 is a transversal cross-sectional view of the controllable ultrasound crystal beacon portion, section II—II, of FIG. 4.

FIG. 8 shows a transversal cross-sectional view of the controllable ultrasound crystal beacon portion, section B—B, of FIG. 4. One end of the connecting means 52 is secured to the beacon deployment mechanism 51 secured on the handle 28, while the other end is coupled to the movable crystal beacon 31 through an appropriate support means 53 for transmitting the deployment force from the beacon deployment mechanism 51 to said movable/controllable crystal beacon 31.

After deploying the catheter system of the present invention, the multiple crystal beacons on the reference catheter are positioned either inside the body or outside the body of a patient. Their coordinates are calibrated frequently by emitting ultrasound signals from said beacons to be received by a calibration system means which is external of the body and is connected to the baseline data program in a data acquisition computer means. By constantly calibrating the coordinates of the beacons on the reference catheter, the received signals at the receiver beacons can be accurately correlated and input into said data acquisition computer to locate the locator catheter.

In a further embodiment, the locator catheter 8 and the reference catheter 14 comprise a plurality of conducting wires that are disposed inside the lumen of the catheter shaft. The proximal end of said conducting wires is secured to a contact pin of the connector 22 or 29 that is secured at the proximal end of the handle 20 or 28. Therefrom, the conducting wires are connected to an external device or data acquisition means for analyzing the signal data from the ultrasound crystals.

The locator catheter 8 further comprises a steering mechanism at the handle for controlling the deflection of said distal tip section having at least one electrode and one ultrasound crystal. Usually a rotating ring or a push-pull plunger 37, such as the one shown in FIG. 2, is employed in the steering mechanism 23. In another embodiment, the steerable ablation catheter comprises a bidirectional deflection or multiple curves deflection of the tip section. One end of the steering wire is attached at certain point of the tip section of said catheter shaft. The other end is attached to the steering mechanism at the handle. The steering mechanism on a steerable catheter or device is well known to those who are skilled in the art. In another embodiment, the steering mechanism 23 at the handle 20 comprises means for providing a plurality of deflectable curves on the distal tip section 16 of the catheter shaft 15.

In an additional embodiment, the ablation version of the locator catheter of this invention further comprises a temperature sensing and close-loop temperature control mechanism for the at least one electrode having a temperature sensor at the tissue contact site of the electrode. The location of the temperature sensor is preferably in the very proximity of the electrodes. In a still further embodiment, a method for operating an ablation catheter further comprises a programmed temperature control mechanism for independently controlling the delivery of RF energy of each electrode of the ablation catheter.

In another particular embodiment, the material for the electrodes may consist of conductive metals such as platinum, iridium, gold, tungsten, silver, stainless steel, Nitinol, or an alloy of their mixture.

A method for operating a catheter system to contact a target tissue in a heart chamber for an electrophysiology study, the catheter system comprising a locator catheter comprising a catheter shaft having a distal tip section, a distal end, a proximal end and at least one lumen extending therebetween, wherein at least one electrode is secured at said distal tip section; a handle attached to the proximal end of said catheter shaft; an ultrasound crystal secured on the catheter shaft proximal to the distal end; a connector secured to the proximal end of said handle; and a reference catheter comprising at least three ultrasound crystal beacons which have pre-determined locations with reference to an external locating calibration system, wherein at least one beacon is movable and controllable by a beacon deployment mechanism at the handle and said ultrasound beacons can emit and receive ultrasound signals; the method comprising the steps of: percutaneously introducing the reference catheter under non-deployed state through a blood vessel to the heart chamber; deploying the catheter to position the at least three ultrasound crystal beacons; locating the at least three ultrasound crystal beacons in reference to an external calibration system; constantly calibrating the location of the crystal beacons on the reference catheter percutaneously introducing the locator catheter through a blood vessel to the heart chamber; deflecting the distal section of said locator catheter about a transverse axis to position the tip section; determining the coordinates of the locator catheter; and intimately contacting the electrode with the target tissue for an electrophysiology study.

The catheter system of the present invention has several significant advantages over known catheters or electrophysiology techniques. In particular, the catheter system with ultrasound locating capabilities and with at least one movable ultrasound crystal beacon result in an effective electrophysiology procedure without undesired side effects of using a conventional x-ray imaging system.

From the foregoing, it should now be appreciated that an improved catheter system having an ultrasound locating capabilities has been disclosed for ablation and/or mapping electrophysiology procedures, including endocardial, epicardial, or body tissue and drug delivery operations for tumor or cancer management. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A catheter system comprising:
    a locator catheter comprising a catheter shaft having a distal tip section, a distal end, a proximal end and at least one lumen extending therebetween, wherein at least one electrode is secured at said distal tip section; a handle attached to the proximal end of said catheter shaft; an ultrasound crystal secured on the catheter shaft proximal to the distal end for transmitting ultrasound signals; a connector secured to the proximal end of said handle;
    a reference catheter comprising at least three ultrasound crystal beacons for receiving the ultrasound signals transmitted from the ultrasound crystal secured to the locator catheter, wherein at least one beacon is movable on said reference catheter and controllable by a beacon deployment mechanism at the handle, said beacons having coordinates that are pre-set with reference to an external location calibration system, wherein said beacons can emit and receive ultrasound signals;
    said external location calibration system for receiving signals from the crystal beacons and constantly calibrating the coordinates of the beacons on the reference catheter; and
    a data acquisition computer connected to the location calibration system for determining the location of the locator catheter.

2. The catheter system of claim 1, wherein said ultrasound crystal beacons on the reference catheter are made of piezoelectric materials.

3. The catheter system of claim 2, wherein the shape of said ultrasound crystal beacons on the reference catheter is selected from the group consisting of a cylinder, a donut, a ring, a spiral, and a mesh.

4. The catheter system as in claim 3 further comprising a steering mechanism at the handle for controlling the steering of the distal tip section of said locator catheter.

5. The catheter system of claim 4, wherein said steering mechanism provides a plurality of deflectable curves on the distal tip section of said locator catheter.

6. The catheter system of claim 3, wherein the at least one electrode is selected from the group consisting of a cylindrical tip electrode, a ring electrode, a spiral electrode, and a mesh electrode.

7. The catheter system as in claim 3, further comprising said reference catheter being located outside the body of a patient.

8. The catheter system as in claim 3, further comprising said reference catheter being located inside the body of a patient, wherein said reference catheter comprises: a delivery shaft having a distal end, a proximal end, and at least one lumen extending therebetween; a handle attached to the proximal end of said delivery shaft; a connector secured to the proximal end of said handle; and a spiral element being located within the delivery shaft under non-deployed state.

9. The catheter system as in claim 6, further comprising a material of said electrode being selected from the group of platinum, iridium, gold, silver, tungsten, stainless steel, and Nitinol.

10. A method for operating a catheter system to contact a target tissue in a heart chamber for an electrophysiology study, the catheter system comprising a locator catheter comprising a catheter shaft having a distal tip section, a distal end, a proximal end and at least one lumen extending therebetween, wherein at least one electrode is secured at said distal tip section; a handle attached to the proximal end of said catheter shaft; an ultrasound crystal secured on the catheter shaft proximal to the distal end; a connector secured to the proximal end of said handle; and a reference catheter comprising at least three ultrasound crystal beacons which have pre-determined locations with reference to an external locating calibration system, wherein at least one beacon is movable on said reference catheter and controllable by a beacon deployment mechanism at the handle and said ultrasound beacons can emit and receive ultrasound signals;

the method comprising the steps of: percutaneously introducing the reference catheter under non-deployed state through a blood vessel to the heart chamber; deploying the catheter to position the at least three ultrasound crystal beacons; locating the at least three ultrasound crystal beacons in reference to an external calibration system; constantly calibrating the location of the crystal beacons on the reference catheter; percutaneously introducing the locator catheter through a blood vessel to the heart chamber; deflecting the distal section of said locator catheter about a transverse axis to position the tip section; determining the coordinates of the locator catheter; and intimately contacting the electrode with the target tissue for an electrophysiology study.

11. The method for operating a catheter system to contact a target tissue in a heart chamber for an electrophysiology study as in claim 10, the catheter system further comprising a RF generator, wherein radiofrequency current is delivered to the target tissue through the at least one electrode.

12. The method for operating a catheter system to contact a target tissue in a heart chamber for an electrophysiology study as in claim 10, wherein said ultrasound crystal beacons on the reference catheter are made of piezoelectric materials.

13. The method for operating a catheter system to contact a target tissue in a heart chamber for an electrophysiology study as in claim 10, wherein the shape of said ultrasound crystal beacons on the reference catheter is selected from the group consisting of a cylinder, a donut, a ring, a spiral, and a mesh.

14. The method for operating a catheter system to contact a target tissue in a heart chamber for an electrophysiology study as in claim 10, further comprising a steering mechanism at the handle of the locator catheter for controlling the steering of the distal tip section of said locator catheter.

15. The method for operating a catheter system to contact a target tissue in a heart chamber for an electrophysiology study as in claim 14, wherein said steering mechanism provides a plurality of deflectable curves on the distal tip section of said locator catheter.

16. The method for operating a catheter system to contact a target tissue in a heart chamber for an electrophysiology study as in claim 10, wherein the at least one electrode is selected from the group consisting of a cylindrical tip electrode, a ring electrode, a spiral electrode, and a mesh electrode.

* * * * *